United States Patent
Jordfald et al.

(10) Patent No.: US 6,471,653 B1
(45) Date of Patent: Oct. 29, 2002

(54) TRANSESOPHAGEAL ULTRASOUND PROBE WITH MOTOR IN THE TIP FOR SCAN-PLANE ROTATION

(75) Inventors: Dag Jordfald, Horten (NO); Jon Ronander, Tonsberg (NO); Jonathan Edvard Snyder, Park City, UT (US); Jiayu Chen, Palo Alto, CA (US); Joseph E. Piel, Jr., Scotia, NY (US); Karl Jonsberg, Tonsberg (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/705,244

(22) Filed: Nov. 2, 2000

(51) Int. Cl.⁷ .................................................. A61B 8/12
(52) U.S. Cl. ..................................................... 600/462
(58) Field of Search ................................ 600/437, 446, 600/459, 462–463

(56) References Cited

U.S. PATENT DOCUMENTS

| | | | |
|---|---|---|---|
| 4,974,590 A | | 12/1990 | Saito |
| 4,977,898 A | * | 12/1990 | Schwarzschild et al. ...... 73/623 |
| 5,020,539 A | | 6/1991 | Yokoi |
| 5,085,221 A | * | 2/1992 | Ingebrigtsen et al. ......... 73/633 |
| 5,467,779 A | * | 11/1995 | Smith et al. ................. 600/446 |
| 5,469,852 A | * | 11/1995 | Nakamura et al. ........... 600/463 |
| 5,562,096 A | * | 10/1996 | Hossach et al. .............. 600/446 |
| 5,771,896 A | * | 6/1998 | Sliwa, Jr. et al. ........... 600/463 |
| 5,884,627 A | | 3/1999 | Wakabayashi |
| 5,980,462 A | | 11/1999 | Maruta |
| 5,993,380 A | | 11/1999 | Yabe |

* cited by examiner

Primary Examiner—Francis J. Jaworski
(74) Attorney, Agent, or Firm—McAndrews, Held & Malloy, Ltd.; Peter J. Vogel; Michael A. Dellapenna

(57) ABSTRACT

A transesophageal ultrasound probe allowing for scan-plane rotation comprises an endoscope with a probe head connected to the distal end of the endoscope. A transducer is secured to the probe head. A transfer mechanism is connected to the transducer. A motor at the distal end of the endoscope is connected to the transfer mechanism. Finally, an electrical wire is connected to the motor. The transesophageal ultrasound probe uses a motor in the tip of the transesophageal ultrasound probe for scan-plane rotation.

14 Claims, 1 Drawing Sheet

FIG. 2     FIG. 3     FIG. 4

TRANSESOPHAGEAL ULTRASOUND PROBE WITH MOTOR IN THE TIP FOR SCAN-PLANE ROTATION

BACKGROUND OF THE INVENTION

This invention is directed to transesophageal echocardiography (TEE) probes used for imaging human organs, particularly the heart. TEE probes are well known in the art and comprise an ultrasonic transducer mounted at the end of a semi-flexible endoscope. The endoscope typically has an articulation section at its distal end that allows the operator to rotate or move the distal end of the endoscope such that the ultrasonic transducer is optimally positioned for imaging the relevant organ. Movement of the articulation section is effected in a controlled manner through controls disposed on a handle located on the proximal end of the endoscope. The semi-flexible nature of the endoscope enables physicians or clinicians to introduce the ultrasonic transducer through the esophagus of a patient to a position where the heart or other relevant structure can be ultrasonically imaged.

Early prior TEE probes permitted only single plane scanning. Operators of these early TEE probes would rotate or move the probe back and forth such that the beam of the ultrasonic transducer would scan over a given scan plane. Although this generation of TEE probe could provide the operator with a single plane scan of a particular organ of interest, it was unable to provide a multi-plane scan. Subsequent TEE probes used two transducers to permit bi-plane scanning in two fixed orientations.

Prior TEE probes were subsequently improved to permit ultrasonic scanning in freely selectable multiple scan planes. This multi-plane scanning was accomplished by mechanically rotating the ultrasonic transducer of the TEE probe from the proximal end of the probe. Mechanical rotation of the ultrasonic transducer was accomplished with a mechanical linkage that extended from the proximal end of the TEE probe to the ultrasonic transducer located at the distal end of the probe. The types of mechanical linkages used in these prior devices are well known in the art, and included the use of either a push/pull wire or a flexible axle. Operators of these prior TEE probes could manipulate the mechanical linkage, and thereby also the scan plane of the ultrasonic transducer, through a handle located at the proximal end of the TEE probe. The handle would use a mechanical transfer mechanism (for example, a mechanical wheel) or motor to manipulate the mechanical linkage of the TEE probe, and thereby provide a multi-plane ultrasonic scan of the organ of interest.

However, the use of mechanical linkages in prior TEE probes limited the accuracy of the scan-plane angle that was measured and indicated at the handle of the probe. This was due primarily to the mechanical hysteresis and spring action effects that resulted from using a mechanical linkage to rotate the ultrasonic transducer. Further, the mechanical nature of the linkages made them vulnerable to failure and represented a negative contribution to the reliability of prior TEE probes. In short, the detrimental effect on scan-plane measurement accuracy associated with using mechanical linkages in TEE probes, as well as decreased reliability, was an undesired characteristic and limitation of prior TEE probes.

Therefore, there is a need for a TEE probe that addresses the prior problems and limitations associated with using a mechanical linkage to rotate a transducer for obtaining multi-plane ultrasonic scans of internal organs.

BRIEF SUMMARY OF THE INVENTION

In a preferred embodiment of the invention, a transesophageal ultrasound probe allowing for scan-plane rotation includes an endoscope with a probe head connected to a distal end of the endoscope. A transducer is secured to the probe head, a transfer mechanism is connected to the transducer, and a motor at the distal end of the endoscope is connected to the transfer mechanism. An electrical wire is connected to the motor and extends to the proximal end of the transesophageal ultrasound probe. The configuration of the motor, the transfer mechanism, and the transducer may be changed in a number of ways to achieve varying performance characteristics. Preferably, the motor, the transfer mechanism, and the transducer are all disposed within the probe head.

In an alternative embodiment, a transesophageal ultrasound probe allowing for scan-plane rotation includes an endoscope with a probe head connected to a distal end of the endoscope. A transducer is secured within the interior of the probe head. Further, a transfer mechanism is secured within the interior of the probe heat and connected to the transducer. Also, a motor is secured within the interior of the probe head and connected to the transfer mechanism. Finally, an electrical wire is connected to the motor and extends to the proximal end of the transesophageal ultrasound probe.

The preferred embodiment has a number of advantages. In particular, the present invention uses a motor in the distal tip of the transesophageal ultrasound probe to allow a clinician to alter the scan-plane of the transducer at will by rotating the transducer around an axis perpendicular to the transducer surface through the use of a transfer mechanism connected to the transducer. The motor is powered through an electrical wire, thereby eliminating the need for the mechanical linkages of prior devices. Other features and advantages of the invention will became apparent from the description that follows.

BRIEF DESCRIPTION OF THE DRAWINGS

Additional objects and features of the invention will appear from the following description in which the preferred embodiments are set forth in conjunction with the accompanying drawings.

FIG. 2 is one embodiment of a drive solution for a transesophageal ultrasound probe allowing for scan-plane rotation utilizing a ratchet mechanism.

FIG. 3 is an alternative embodiment of a drive solution for a transesophageal ultrasound probe allowing for scan-plane rotation utilizing a rotary motor.

FIG. 4 is an alternative embodiment of a drive solution for a transesophageal ultrasound probe allowing for scan-plane rotation utilizing a piezo motor.

DETAILED DESCRIPTION OF THE INVENTION

Figure 1:
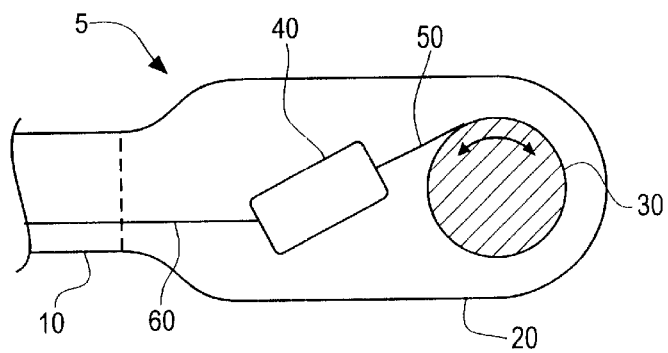
FIG. 1 is cross-section of the distal end of one embodiment of a transesophageal ultrasound probe allowing for scan-plane rotation.
Figure 1:
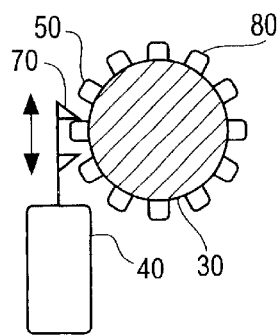
Figure 1:
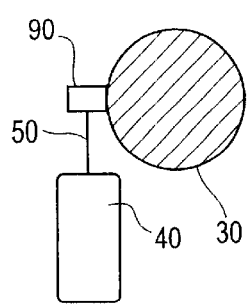
Figure 1:
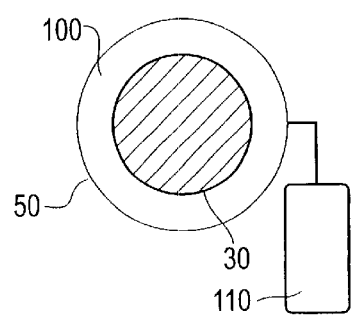

Turning to FIG. 1, one embodiment of a transesophageal ultrasound probe allowing for scan-plane rotation 5 is illustrated. The transesophageal ultrasound probe allowing for scan-plane rotation 5 includes an endoscope 10 with a probe heat 20 connected to the distal end of the endoscope 10. The probe head 20 includes a transducer 30, a motor 40, a transfer mechanism 50, and an electrical wire 60, all of which are secured within the probe head 20.

The transfer mechanism 50 is connected to the transducer 30 in a manner that allows the transducer 30 to be rotated. Any number of different transfer mechanisms 50 known in the art may be used to rotate the transducer 30. The rotation of the transducer 30 allows for rotation of the ultrasonic scan-plane, as illustrated in FIG. 1. The motor 40 of the probe head 20 is connected to the transfer mechanism 50 and provides power or motive force to the transfer mechanism 50. The electrical wire 60 is connected to the motor 40 and provides an electrical conduit for powering the motor 40. The electrical wire 60 extends from the proximal end of the transesophageal ultrasound probe allowing for scan-plane rotation 5 to the motor 40 located at the distal end of the transesophageal ultrasound probe allowing for scan-plane rotation 5 and transmits power (e.g., electrical) to the motor 40.

Turning to FIG. 2, an embodiment of the transfer mechanism 50 of the transesophageal ultrasound probe allowing for scan-plane rotation 5 is illustrated which uses a ratchet mechanism to rotate the transducer 30. In this embodiment, the transfer mechanism 50 includes a ratchet 70 and a plurality of gear teeth 80 secured about the transducer 30. The ratchet 70 is connected to the motor 40. The motor 40 is designed to move the ratchet 70 in a manner that permits the transducer 30 to be rotated in either a clockwise or counterclockwise direction. The rotation of the transducer 30 is effected through the dynamic interaction of the ratchet 70 and the plurality of gear teeth 80 secured about the transducer 30.

In a preferred embodiment, the plurality of gear teeth 80 is uniformly distributed about the transducer 30. However, the dimensions of the plurality of gear teeth 80 may be varied in a number of different ways well known in the art to achieve the desired drive characteristics. For example, in order to achieve sufficiently small increments of rotation of the transducer 30 it may be necessary for the plurality of gear teeth 80 to comprise geared helical, worm, bevel, or hypoid teeth.

Turning to FIG. 3, an alternative embodiment of the transfer mechanism 50 of the transesophageal ultrasound probe allowing for scan-plane rotation 5 is illustrated which uses a rotary motor 40 to rotate the transducer 30. In this embodiment, the transfer mechanism 50 may include a plurality of cogwheels 90 connected to the rotary motor 40. The plurality of cogwheels 90 is secured to the transducer 30 in a manner that allows rotation of the transducer 30 in either a clockwise or counterclockwise direction. The rotary motor 40 may be a DC, an AC, or a step motor. In a further alternative embodiment, the plurality of cogwheels 90 may comprise a worm screw or a driving belt as the means for transferring movement to the transducer 30. The rotary motors 40 described in this embodiment are well known in the art and commercially available through a number of companies, including through RMB, S. A.'s Smoovy product line of micro drives.

Turning to FIG. 4, an alternative embodiment of the transfer mechanism 50 of the transesophageal ultrasound probe 5 is illustrated. In this embodiment, the motor 40 is a piezo motor 110 and the transfer mechanism 50 includes a stationary piezo drive 100 secured to the transducer 30. The stationary piezo drive 100 may be secured to the transducer 30 in a variety of ways, including by clamping the stationary piezo drive 100 to the transducer 30. The stationary piezo drive 100 is driven by the piezo motor 110. In one embodiment, the stationary piezo drive 100 may be a pre-selective piezo ring comprising a ring of piezoelectric material that is divided into discrete and separate fingers on the inside of the ring of peizo-electric material. The fingers are then connected to electrodes and electronics that permit the transducer 30 to be rotated through movement of the fingers. The use of piezo motors and stationary piezo drives to effect movement is well known in the art. It should be appreciated that the precise geometric arrangement of the piezo motor 110 and the stationary piezo drive 100 may be varied to obtain a particular desired rotational characteristic for the transducer 30 without departing from the scope of the invention.

In one embodiment, the piezo motor 110 may be a separate component that transfers movement to the transducer 30 through the stationary piezo drive 100 by mechanical means, such as those typically used in conjunction with a rotary motor. In an alternative embodiment, the piezo motor 110 may be integrated with the transducer 30 to form an assembly, with the stationary piezo drive 100 comprising a ring secured around the circumference of the transducer 30 and being driven by the piezo motor 110. In a further alternative embodiment, the piezo motor 110 may be located underneath the transducer 30 to accommodate the use of a large piezo motor 110. In this instance, the piezo motor 110 is preferably positioned such that motion is transferred directly on an axis extending through the center of the rear of the transducer 30.

The present invention thereby provides a transesophageal ultrasound probe allowing for scan-plane rotation 5. The scan-plane rotation is achieved by rotating the transducer with a motor located at the distal tip of the transesophageal ultrasound probe. The motor may be powered electrically, pneumatically, or hydraulically. Also, the orientation between the motor and the transducer may be varied as necessary. The detrimental effect on scan-plane measurement accuracy and device reliability is, thus, eliminated by using the motor located at the distal tip of the transesophageal ultrasound probe to rotate the transducer instead of using the mechanical linkages of prior transesophageal ultrasound probe.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A transesophageal ultrasound probe allowing for scan-plane rotation comprising:
    an endoscope;
    a probe head connected to a distal end of the endoscope;
    a transducer secured to the probe head;
    a transfer mechanism secured about an outermost circumference of the transducer;
    a single motor at the distal end of the endoscope connected to the transfer mechanism; and
    an electrical wire connected to the motor.

2. The transesophageal ultrasound probe allowing for scan-plane rotation of claim 1 wherein the transducer, the transfer mechanism, and the motor are disposed entirely within the probe head.

3. The transesophageal ultrasound probe allowing for scan-plane rotation of claim 1 wherein the electrical wire extends from the motor to the proximal end of the transesophageal ultrasound probe.

4. The transesophageal ultrasound probe allowing for scan-plane rotation of claim 1 wherein the motor is a rotary motor.

5. The transesophageal ultrasound probe allowing for scan-plane rotation of claim 1 wherein the motor is a piezo motor and the transfer mechanism is a stationary piezo drive secured about the circumference of the transducer.

6. The transesophageal ultrasound probe allowing for scan-plane rotation of claim 5 wherein the piezo motor is positioned underneath the transducer and wherein the piezo motor and the transducer share a common central axis.

7. The transesophageal ultrasound probe allowing for scan-plane rotation of claim 1 wherein the transfer mechanism comprises a ratchet connected to a plurality of gear teeth secured about the circumference of the transducer.

8. A transesophageal ultrasound probe allowing for scan-plane rotation comprising:

an endoscope;

a probe head connected to a distal end of the endoscope;

a transducer secured to the probe head;

a transfer mechanism secured about an outermost circumference of the transducer;

a single motor at the distal end of the endoscope connected to the transfer mechanism; and an electrical wire connected to the motor and extending to the proximal end of the transesophageal ultrasound probe.

9. The transesophageal ultrasound probe allowing for scan-plane rotation of claim 8 wherein the transducer, the transfer mechanism, and the motor are disposed entirely within the probe head.

10. The transesophageal ultrasound probe allowing for scan-plane rotation of claim 8 wherein the motor is a piezo motor.

11. The transesophageal ultrasound probe allowing for scan-plane rotation of claim 10 wherein the piezo motor is positioned underneath the transducer and wherein the piezo motor and the transducer share a common central axis.

12. A transesophageal ultrasound probe allowing for scan-plane rotation comprising:

an endoscope;

a probe head connected to a distal end of the endoscope;

a transducer secured within the interior of the probe head;

a transfer mechanism secured within the interior of the probe head and secured about an outermost circumference of the transducer;

a single motor secured within the interior of the probe head and connected to the transfer mechanism; and an electrical wire connected to the motor and extending to the proximal end of the transesophageal ultrasound probe.

13. The transesophageal ultrasound probe allowing for scan-plane rotation of claim 12 wherein the motor is a rotary motor.

14. The transesophageal ultrasound probe allowing for scan-plane rotation of claim 12 wherein the motor is a piezo motor and the transfer mechanism is a stationary piezo drive secured about the circumference of the transducer.

* * * * *